(12) United States Patent
Chen et al.

(10) Patent No.: US 10,098,852 B2
(45) Date of Patent: Oct. 16, 2018

(54) INDICATION OF MONOBENZONE PHARMACEUTICAL COMPOSITION FOR TREATING CANCER

(71) Applicant: LAUNX BIOMEDICAL CO., LTD., Kaohsiung (TW)

(72) Inventors: Chiu-Hung Chen, Kaohsiung (TW); Show-Mei Chuang, Taichung (TW); Tzong-Der Way, Kaohsiung (TW); Nai-Wan Hsiao, Taichung (TW)

(73) Assignee: LAUNX BIOMEDICAL CO., LTD., Kaohsiung (TW)

( * ) Notice: Subject to any disclaimer, the term of this patent is extended or adjusted under 35 U.S.C. 154(b) by 0 days.

(21) Appl. No.: 15/521,540

(22) PCT Filed: Oct. 23, 2015

(86) PCT No.: PCT/CN2015/092617
§ 371 (c)(1),
(2) Date: Apr. 24, 2017

(87) PCT Pub. No.: WO2016/062265
PCT Pub. Date: Apr. 28, 2016

(65) Prior Publication Data
US 2017/0304218 A1    Oct. 26, 2017

Related U.S. Application Data

(60) Provisional application No. 62/068,298, filed on Oct. 24, 2014.

(51) Int. Cl.
| | | |
|---|---|---|
| *A01N 31/14* | (2006.01) | |
| *A61K 31/075* | (2006.01) | |
| *A61K 31/085* | (2006.01) | |

(52) U.S. Cl.
CPC ............................ *A61K 31/085* (2013.01)

(58) Field of Classification Search
USPC ........................................................ 514/721
See application file for complete search history.

(56) References Cited

U.S. PATENT DOCUMENTS

2012/0315304 A1* 12/2012 Westerhof .............. A61K 31/05
424/400

\* cited by examiner

*Primary Examiner* — Marcos L Sznaidman
(74) *Attorney, Agent, or Firm* — Liang Legal Group, PLLC

(57) ABSTRACT

A method for treating a cancer includes administering to a subject in need thereof a therapeutically effective amount of a pharmaceutical composition comprising Monobenzone or a pharmaceutical acceptable salt thereof. The cancer is selected from pleural-related cancer, abdominal-related cancer, endocrine-related cancer, gastrointestinal tract-related cancer, osteosarcoma, and skin cancer. The pleural-related cancer is lung cancer. The abdominal-related cancer is selected from bladder cancer, cervical cancer, and kidney cancer. The endocrine-related cancer is selected from prostate cancer, breast cancer, and ovarian cancer. The gastrointestinal tract-related cancer is selected from gastric cancer, hepatic cancer, colorectal cancer, pancreatic cancer, and tongue cancer.

2 Claims, 3 Drawing Sheets

INDICATION OF MONOBENZONE PHARMACEUTICAL COMPOSITION FOR TREATING CANCER

CROSS-REFERENCE TO RELATED APPLICATIONS

This is a National Phase Application filed under 35 U.S.C. 371 as a national stage of PCT/CN2015/092617 filed Oct. 23, 2015, an application claiming the benefit under 35 USC 119(e) to the following U.S. Provisional Applications No. 62/068,298 filed Oct. 24, 2014, the content of each of which is hereby incorporated by reference in its entirety.

FIELD OF THE INVENTION

The present invention related to a new indication of Monobenzone pharmaceutical composition, especially related to inhibition effect of Monobenzone pharmaceutical composition on a variety of cancer cells.

BACKGROUND OF THE INVENTION

Monobenzone is a topical bleaching agent for the treatment of hyperpigmentation, such as various spots, age spots, and melanoma. The effect of monobenzone is obvious for the above-mentioned effect. Monobenzone can decompose the melanin in the skin to prevent the generation of melanin in the skin, so that the skin would restore the naturally original skin color. In the meantime. Monobenzone does not destroy melanoma cells. Toxicity of monobenzone is light, and monobenzone is usually made as ointment or liniment as pharmaceuticals. Monobenzone is approved by FDA and accumulated a huge data of drug use and drug mechanism research.

Due to the differences of the clinical use, there is no research present that the Monobenzone has any potential to inhibit cancer cell.

On the other side, cancer is the most popular disease cause of death in the world. The cancer patients are gradually increase yearly, therefore the treatment method of the cancer has become an important issue. The medical treatments of cancer can be classified as surgical treatment, radiation therapy, chemotherapy and target therapy. Generally, the cancer drug, whether chemotherapy drug or target therapy drug, is to inhibit cancer cells duplication and split to prevent the tumor growth and metastasis. Averagely, only about five of 10,000 new drugs can successfully enter the phase I of clinical trials. Furthermore, if the cancer patients happen the drug resistance, that would reduce the effectiveness of the drugs and result in the medical treatment failure. In other words, the new drug development is very difficult.

Therefore, it is a very urgent and important issue that how to develop anti-cancer drugs quickly and reduce the probability of clinical failure for treating various cancers.

SUMMARY OF THE INVENTION

In order to solve the above problems, the present invention provides the development of new cancer clinical indications of Monobenzone.

Accordingly, the present invention provides a new indication of Monobenzone. The experimental results showed that the Monobenzone had no toxicity or had little toxicity to normal cells in the present invention. However, the selective effect of Monobenzone between normal cells and cancer cells need to be identified.

The present invention provides a pharmaceutical composition of Monobenzone for treating cancer. The pharmaceutical composition is composed of effective dose of Monobenzone and a pharmaceutical acceptable salt.

In one embodiment of the present invention, the cancer is selected from pleural-related cancer, abdominal-related cancer, endocrine-related cancer, gastrointestinal tract-related cancer.

In one embodiment of the present invention, the cancer is selected from osteosarcoma, skin cancer and blood cancer.

In one embodiment of the present invention, the pleural-related cancer is lung cancer.

In one embodiment of the present invention, the abdominal-related cancer is selected from bladder cancer, and cervical cancer.

In one embodiment of the present invention, the endocrine-related cancer is selected from prostate cancer, breast cancer, and ovarian cancer.

In one embodiment of the present invention, the gastrointestinal tract-related cancer is selected from gastric cancer, hepatic cancer, colorectal cancer, pancreatic cancer, and tongue cancer.

In one embodiment of the present invention, the effective dose of Monobenzone is from 20 mg/kg/day to 500 mg/kg/day.

DETAILED DESCRIPTION OF THE INVENTION

Cell Culture

Figure 1:
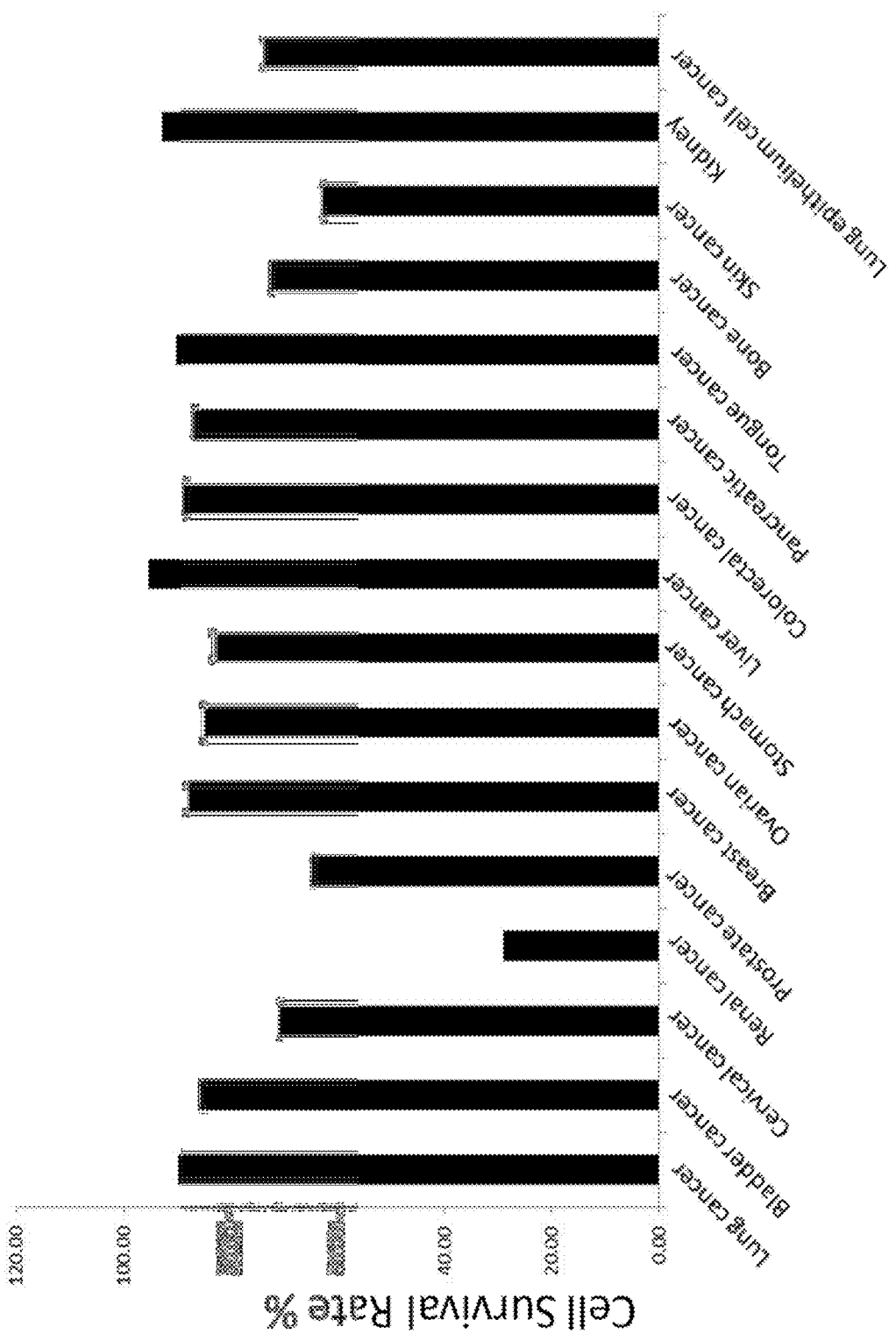
FIG. 1 shows the results of the inhibitory effect of the different cancer cells by Monobenzone.

Subculture the different types of cancer cells. The cancer cells lines includes lung cancer, gastric cancer, hepatic cancer, colon cancer, skin cancer, cervical cancer, prostate cancer, bladder cancer, breast cancer, leukemia, pancreatic cancer, ovarian cancer, tongue cancer, osteosarcoma, and renal cancer. The normal cells used in the control group included kidney cell line (HEK293) and human bronchial epithelial cell line BEAS-2B. (as shown in Table 1).

Cancer cell lines were cultured in different culture medium according to different characteristics (as shown in Table 1). The cell numbers were counted and reseed as $2 \times 10^6$ in cell culture plate/flask. Then, the culture medium was added to a volume of 10 ml, and the cells were cultured for 2-3 days. Then, the cells were suspended for loading into 96-well plates. The cell number was 3000/well and the volume of the culture medium was 100 µl each well.

TABLE 1

Cancer cell lines and the culture medium

| No | Cancer type | Cancer cell type | Culture medium |
|---|---|---|---|
| 1 | lung cancer | H1650 (lung adenocarcinoma) | RPMI-1640 |
|   |   | A549 (lung adenocarcinoma) | DMEM |
| 2 | gastric cancer | AGS (Gastric Adenocarcinoma) | RPMI-1640 |
|   |   | MKN-45 (Gastric Adenocarcinoma) | RPMI-1640 |
| 3 | hepatic cancer | HepG2 (hepatocellular carcinoma) | DMEM |
|   |   | Hep3B (hepatocellular carcinoma) | DMEM |
| 4 | colon cancer | HCT116 (p53+) (colorectal carcinoma) | DMEM |
|   |   | LoVo(Colorectal Adenocarcinoma) | DMEM |
| 5 | skin cancer | A375 (amelanotic melanoma) | DMEM |
|   |   | BCC (basal cell carcinoma) | DMEM |
| 6 | cervical cancer | HeLa (Cervix Adenocarcinoma) | DMEM |
|   |   | C-33A (Cervical carcinoma) BCRC60554 | MEM |
| 7 | prostate cancer | PC3 (p53−)(Prostate adenocarcinoma) | DMEM |
|   |   | LNCaP clone FGC (LNCap.FGC) | RPMI-1640 |
| 8 | bladder cancer | 8301 (urinary bladder carcinoma) | RPMI-1640 |
|   |   | T24 | RPMI-1640 |
| 9 | breast cancer | MCF7 (Mammary Gland, Adenocarcinoma) | DMEM |
|   |   | MDA-MB-231 (Mammary Gland, Adenocarcinoma) | DMEM |
| 10 | pancreatic cancer | BxPC-3 | RPMI-1640 |
|   |   | AsPC-1 | RPMI-1640 |
| 11 | ovarian cancer | NIH: OVCAR-3 | RPMI-1640 |
|   |   | TOV-21G | RPMI-1640 |
| 12 | tongue cancer | SAS (Tongue squamous cell carcinoma) | DMEM |
| 13 | osteosarcoma | U-2OS | DMEM |
| 14 | renal cancer | 786-O (Renal adenocarcinoma) BCRC 60243 | RPMI-1640 |
| 15 | normal cell kidney | HEK293 (Kidney) | DMEM |
|   | pulmonary | BEAS-2B (Lung Epithelial) | RPMI-1640 |

Cell Viability Analysis

Removing the original culture medium from 96-well plate. Then add 100 μl of commercially drug at a concentration of 10 μM per well. After 72 hours, add the diluted WST-1 reagent to the well with 100 μl/well, and the diluted WST-1 reagent was acquired from the dilution of 9:1 medium and WST-1 stock reagent. Finally, the total volume of each well was 200 μl/well. Culture the 96-well plate at 37° C. for 30 to 90 minutes. Detecting and calculate the survival rate of each cancer cells with an ELISA reader at OD450 nm. The lower viability of cancer cells represents better inhibition effect via the Monobenzone drug. Otherwise, the higher viability of cancer cells represents worse inhibition effect via the Monobenzone drug.

The Effect of Monobenzone on Different Cancer Cell Lines

The Inhibition Effect of Monobenzone on Pleural-Related Cancer Cells

This inhibition test of Monobenzone on pleural-related cancer cells were using two lung cancer cell lines A549 and H1650. The inhibitory tests of Monobenzone were performed 4 times for each cell lines and then the average value of the inhibitory tests was calculated. The results were shown in Table 2.

TABLE 2

The inhibition effect of Monobenzone on pleural-related cancer cells

|  | 0524-10 min | 0526-10 min | 0529-10 min | 0531-10 min | Average |
|---|---|---|---|---|---|
| A549 | 80.8 | 111.1 | 80.8 | 100.9 | 93.4 |

TABLE 2-continued

The inhibition effect of Monobenzone on pleural-related cancer cells

|  | 1-10 min | 2-20 min | 3-20 min | 4-20 min | Average |
|---|---|---|---|---|---|
| H1650 | 90.1 | 66.6 | 86.7 | 101.8 | 86.3 |

The Inhibition Effect of Monobenzone on Abdominal-Related Cancer Cell Lines

This inhibition test of Monobenzone on abdominal-related cancer cells were using bladder cancer cell lines TSGH and T24 (Table 3), cervical cancer cell lines HeLa and C-33A (Table 4), renal cancer cell line 786-O (Table 5). The inhibitory tests of Monobenzone were performed 4 times for each cell lines and then the average value of the inhibitory tests was calculated. The results were shown in Table 3, Table 4, and Table 5.

TABLE 3

The inhibition effect of Monobenzone on bladder cancer cell lines

|  | 0510-10 min | 0512-10 min | 0515-10 min | 0517-10 min | average |
|---|---|---|---|---|---|
| TSGH | 90.19 | 92.84 | 83.05 | 72.48 | 84.6 |

|  | T24-1-30 min | T24-2-20 min | T24-3-20 min | T24-4-20 min | average |
|---|---|---|---|---|---|
| T24 | 93.5 | 70.4 | 89.4 | 94.7 | 87.0 |

TABLE 4

The inhibition effect of Monobenzone on cervical cancer cell lines

|  | 0524-10 min | 0526-10 min | 0529-10 min | 0531-10 min | average |
|---|---|---|---|---|---|
| HeLa | 82.8 | 72.8 | 82.7 | 81.9 | 80.1 |
|  | 1 | 2 | 3 | 4 | average |
| C-33A | 57.9 | 66.2 | 61.0 | 64.3 | 62.3 |

TABLE 5

The inhibition effect of Monobenzone on renal cancer cell line

|  | 0524-10 min | 0526-10 min | 0529-10 min | 0531-10 min | average |
|---|---|---|---|---|---|
| 786-O | 39.8 | 32.4 | 21.2 | 23.4 | 29.2 |

The Inhibition Effect of Monobenzone on Endocrine-Related Cancer Cell Lines

This inhibition test of Monobenzone on endocrine-related cancer cells were using prostate cancer cell lines PC-3 and LNCap (Table 6), breast cancer cell lines MCF7 and MDA-MB-231 (Table 7), and ovarian cancer cell lines NIH-OVCAR-3 and TOV-21G (Table 8). The inhibitory tests of Monobenzone were performed 4 times for each cell lines and then the average value of the inhibitory tests was calculated. The results were shown in Table 6, Table 7, and Table 8.

TABLE 6

The inhibition effect of Monobenzone on prostate cancer cell lines

|  | PC-3-0524-10 min | PC-3-0526-10 min | PC-3-0529-10 min | PC-3-0531-10 min | average |
|---|---|---|---|---|---|
| PC-3 | 57.02 | 70.58 | 63.23 | 58.99 | 62.5 |
|  | LNCap-1-10 min | LNCap-2-20 min | LNCap-3-20 min | LNCap-4-20 min | average |
| LNCap | 65.5 | 52.7 | 81.6 | 71.6 | 67.9 |

TABLE 7

The inhibition effect of Monobenzone on breast cancer cell lines

|  | 0612-10 min | 0614-10 min | 0616-10 min | 0619-10 min | average |
|---|---|---|---|---|---|
| MCF7 | 107.11 | 88.8 | 80.6 | 106.3 | 95.7 |
|  | 0612-10 min | 0614-10 min | 0616-10 min | 0619-10 min | average |
| MDA-MB-231 | 91.3 | 67.6 | 69.6 | 91.95 | 80.1 |

TABLE 8

The inhibition effect of Monobenzone on ovarian cancer cell lines

|  | 7-3-30 min | 7-4-30 min | 7-7-30 min | -4-30 min | average |
|---|---|---|---|---|---|
| NIH-OVCAR-3 | 88.3 | 96.6 | 88.3 | 92.7 | 91.5 |
|  | 7-3-30 min | 7-4-30 min | 7-7-30 min | -4-30 min | average |
| TOV-21G | 93.9 | 78.4 | 69.6 | 71.6 | 78.4 |

The Inhibition Effect of Monobenzone on Gastrointestinal Tract-Related Cancer Cell Lines This inhibition test of Monobenzone on gastrointestinal tract-related cancer cells were using gastric cancer cell lines AGS and MKN-45 (Table 9), hepatic cancer cell lines HepG2 and Hep3B (Table 10), colorectal cancer cell lines HCT116-wt and LoVo (Table 11), pancreatic cancer cell lines AsPC-1 and BxPC-3 (Table 12), tongue cancer cell line SAS (Table 13). The inhibitory tests of Monobenzone were performed 4 times for each cell lines and then the average value of the inhibitory tests was calculated. The results were shown in Table 9, Table 10, Table 11, Table 12 and Table 13.

TABLE 9

The inhibition effect of Monobenzone on gastric cancer cell lines

|  | 0510-10 min | 0512-10 min | 0515-10 min | 0517-10 min | average |
|---|---|---|---|---|---|
| AGS | 85.24 | 51.34 | 62.21 | 74.93 | 68.4 |
|  | 0510-10 min | 0512-10 min | 0515-10 min | 0517-10 min | average |
| MKN-45 | 89.24 | 107.41 | 100.95 | 91.30 | 97.2 |

TABLE 10

The inhibition effect of Monobenzone on hepatic cancer cell lines

|  | 0524-20 min | 0526-20 min | 0529-20 min | 0531-20 min | average |
|---|---|---|---|---|---|
| HepG2 | 88.2 | 85.6 | 90.8 | 74.3 | 84.7 |
|  | 0612-20 min | 0614-20 min | 0616-20 min | 0619-20 min | average |
| Hep3B | 110.6 | 116.2 | 96.8 | 100.6 | 106.1 |

TABLE 11

The inhibition effect of Monobenzone on colorectal cancer cell lines

|  | 0602-30 min | 0605-10 min | 0607-10 min | 0609-10 min | average |
|---|---|---|---|---|---|
| HCT116-wt | 91.12 | 103.66 | 99.94 | 85.3 | 95.0 |
|  | 0616-10 min | 0619-10 min | 0621-10 min | 0623-10 min | average |
| LoVo | 82.29 | 73.94 | 94.7 | 81.3 | 83.0 |

TABLE 12

The inhibition effect of Monobenzone on pancreatic cancer cell lines

|  | 1-7-3-30 min | 1-7-4-30 min | 1-7-7-30 min | 1-4-30 min | average |
|---|---|---|---|---|---|
| AsPC-1 | 88.7 | 116.5 | 81.7 | 93.7 | 95.1 |

|  | 3-7-3-30 min | 3-7-4-30 min | 3-7-7-30 min | 3-4-30 min | average |
|---|---|---|---|---|---|
| BxPC-3 | 57.4 | 100.0 | 70.7 | 86.3 | 78.6 |

TABLE 13

The inhibition effect of Monobenzone on tongue cancercell line

|  | 6-26-10 min | 6-28-10 min | 6-30-10 min | 7-3-10 min | average |
|---|---|---|---|---|---|
| SAS | 97.29 | 59.36 | 89.56 | 115.2 | 90.3 |

The Inhibition Effect of Monobenzone on Other Cancer Cell Lines

This inhibition test of Monobenzone on other cancer cells were using osteosarcoma cell line U2OS (Table 14), skin cancer cell lines A375 and BCC (Table 15). The inhibitory tests of Monobenzone were performed 4 times for each cell lines and then the average value of the inhibitory tests was calculated. The results were shown in Table 14 and Table 15.

TABLE 14

The inhibition effect of Monobenzone on osteosarcoma cancer cell line

|  | 6-26-10 min | 6-28-10 min | 6-30-10 min | 7-3-10 min | average |
|---|---|---|---|---|---|
| U2OS | 69.3 | 66.7 | 73.0 | 81.7 | 72.7 |

TABLE 15

The inhibition effect of Monobenzone on skin cancer cell lines

|  | 0602-30 min | 0605-10 min | 0607-10 min | 0609-10 min | Average |
|---|---|---|---|---|---|
| A375 | 56.7 | 64.8 | 77.3 | 106.8 | 76.4 |

|  | 0602-30 min | 0605-10 min | 0607-10 min | 0609-10 min | Average |
|---|---|---|---|---|---|
| BCC | 48.2 | 59.8 | 38.6 | 53.80 | 50.1 |

The Experiment Design on Control Group

The Inhibition Effect of Monobenzone on Normal Cells

This inhibition test of Monobenzone on normal cells were using normal kidney cell line HEK293 (Table 16), human fibroblast cell line HFW (Table 17), and normal pulmonary epithelial cell line BEAS-2B (Table 18). The inhibitory tests of Monobenzone were performed 4 times for each cell lines and then the average value of the inhibitory tests was calculated The results were shown in Table 16, Table 17 and Table 18.

TABLE 16

The inhibition effect of Monobenzone on normal kidney cell line

|  | 0602-30 min | 0605-30 min | 0607-30 min | 0609-30 min | average |
|---|---|---|---|---|---|
| HEK293 | 82.7 | 99.43 | 97.88 | 91.84 | 93.0 |

TABLE 17

The inhibition effect of Monobenzone on human fibroblast cell line

|  | 0612-10 min | 0614-10 min | 0616-10 min | 0619-10 min | average |
|---|---|---|---|---|---|
| HFW | 119.66 | 74.93 | 68.08 | 79.13 | 85.4 |

TABLE 18

The inhibition effect of Monobenzone on normal pulmonary epithelial cell line

|  | 0510-10 min | 0512-10 min | 0515-10 min | 0517-10 min | average |
|---|---|---|---|---|---|
| BEAS-2B | 84.7 | 79.5 | 74.9 | 56.2 | 73.8 |

This inhibition test results of Monobenzone on all kinds of cancer cells were shown in Table 19. As a result in the experiments of the present invention, Monobenzone has a significant inhibitory effect and specificity on various cancer cells. (FIG. 1)

TABLE 19

Summary of the Effect on different cancer cell lines by Monobenzone

| cancer cell line | Inhibitory effect |
|---|---|
| lung cancer cell | 89.85 |
| bladder cancer cell | 85.80 |
| cervical cancer cell | 71.20 |
| Kidney cancer cell | 29.20 |
| prostate cancer cell | 65.20 |
| breast cancer cell | 87.90 |
| ovarian cancer cell | 84.95 |
| gastric cancer cell | 82.80 |
| hepatic cancer cell | 95.40 |
| colorectal cancer cell | 89.00 |
| pancreatic cancer cell | 86.85 |
| tongue cancer cell | 90.30 |
| osteosarcoma cell | 72.70 |
| skin cancer cell | 63.25 |

Animal Model Test of Gastric Cancer with Dose 100 mg/kg/day and 200 mg/kg/day

In this invention, the female mice were (BALB/cAnN.Cg-Foxn1$^{nu}$/CrlNarl) purchased from National Laboratory Animal Center (Taiwan)). The weight of the mice were 21±1 g. These mice were subcutaneously injected with gastric cancer cells (AGS) and then put these mice into different cages at random. The drug test experiment was divided into three groups, include "control group", "low dose group (100 mg/kg/day)", and "high dose group (200 mg/kg/day)". These mice were then injected test drug intraperitoneally once daily until the tumor size reached 100 mm$^3$. The tumor sizes and body weight were measured twice a week. The tumor sizes were measured and calculated by formula: $(L \times W^2)/2$. L represents the tumor longest length. W represents the tumor shortest diameter. The experiment result is shown in Table 20.

TABLE 20

The inhibitory effect of tumor volume via administered Monobenzone

| | control group | | | | | low dose (100 mg/kg/day) | | | | |
|---|---|---|---|---|---|---|---|---|---|---|
| | weight (g) | longest length mm | width mm | volume mm3 | Tumor volume growth mm3 | weight (g) | longest length mm | width mm | volume mm3 | |
| *First measurement* | | | | | | | | | | |
| A | 18.5 | 7 | 7 | 171.5 | 171.5 | 21 | 8 | 8 | 256 | |
| B | 22 | 8 | 6 | 144 | 144 | 21 | 6 | 7 | 147 | |
| C | 20.5 | 9 | 8 | 288 | 288 | 21 | 7 | 6 | 126 | |
| average | 20.4 | 7.6 | 7 | 189.3 | 189.3 | | | | 176.3333 | |
| *Second measurement* | | | | | | | | | | |
| A | 22 | 7 | 6 | 126 | −45.5 | 20 | 7 | 6 | 126 | |
| B | 20 | 8 | 7 | 196 | 52 | 20 | 6 | 6 | 108 | |
| C | 20 | 9 | 7 | 220.5 | −67.5 | 19 | 5 | 5 | 62.5 | |
| average | 20.6 | 8.4 | 6.8 | 198.5 | 9.2 | | | | 98.83333 | |
| *Third measurement* | | | | | | | | | | |
| A | 23 | 9 | 6 | 162 | 36 | 19.5 | 7 | 6 | 126 | |
| B | 20 | 10 | 8 | 320 | 124 | 19 | 6 | 6 | 108 | |
| C | 21 | 11 | 7 | 269.5 | 49 | 18.5 | 5 | 5 | 62.5 | |
| average | 21.2 | 10 | 6.8 | 235.3 | 36.8 | | | | 98.83333 | |
| *Fourth measurement* | | | | | | | | | | |
| A | 23 | 11 | 7 | 269.5 | 107.5 | 20 | 4 | 3 | 18 | |
| B | 22 | 10 | 6 | 180 | −140 | 21 | 5 | 4 | 40 | |
| C | 23 | 11 | 8 | 352 | 82.5 | 20 | 0 | 0 | 0 | |
| average | 22.4 | | | 233.5 | −1.8 | | | | 19.33333 | |
| *Fifth measurement* | | | | | | | | | | |
| A | 22 | 12 | 8 | 384 | 114.5 | 20 | 4 | 3 | 18 | |
| B | 22 | 11 | 8 | 352 | 172 | 20 | 6 | 4 | 48 | |
| C | 23 | 12 | 9 | 486 | 134 | 21 | 0 | 0 | 0 | |
| average | 22.4 | | | 295.7 | 62.2 | | | | 22 | |

| | low dose (100 mg/kg/day) | high dose (200 mg/kg/day) | | | | |
|---|---|---|---|---|---|---|
| | Tumor volume growth mm3 | weight (g) | longest length mm | width mm | volume mm3 | Tumor volume growth mm3 |
| *First measurement* | | | | | | |
| A | 256 | 20 | 4 | 3 | 18 | 18 |
| B | 147 | 19.5 | 6 | 3 | 27 | 27 |
| C | 126 | 20 | 4 | 4 | 32 | 32 |
| average | 176.3333 | | | | 25.66667 | 25.66667 |
| *Second measurement* | | | | | | |
| A | −130 | 19 | 7 | 5 | 87.5 | 69.5 |
| B | −39 | 20 | 6 | 5 | 75 | 48 |
| C | −63.5 | 19 | 7 | 5 | 87.5 | 55.5 |
| average | −77.5 | | | | 83.33333 | 57.66667 |
| *Third measurement* | | | | | | |
| A | 0 | 20.5 | 7 | 5 | 87.5 | 0 |
| B | 0 | 19 | 5 | 5 | 62.5 | −12.5 |
| C | 0 | 20 | 0 | 0 | 0 | −87.5 |
| average | 0 | | | | 50 | −33.3333 |
| *Fourth measurement* | | | | | | |
| A | −108 | 20 | 0 | 0 | 0 | −87.5 |
| B | −68 | 20 | 0 | 0 | 0 | −62.5 |
| C | −88 | 21 | 0 | 0 | 0 | 0 |
| average | −88 | | | | 0 | −50 |
| *Fifth measurement* | | | | | | |
| A | 0 | 20 | 0 | 0 | 0 | 0 |
| B | 8 | 20 | 0 | 0 | 0 | 0 |
| C | 0 | 21 | 0 | 0 | 0 | 0 |
| average | 2.666667 | | | | 0 | 0 |

Figure 2:
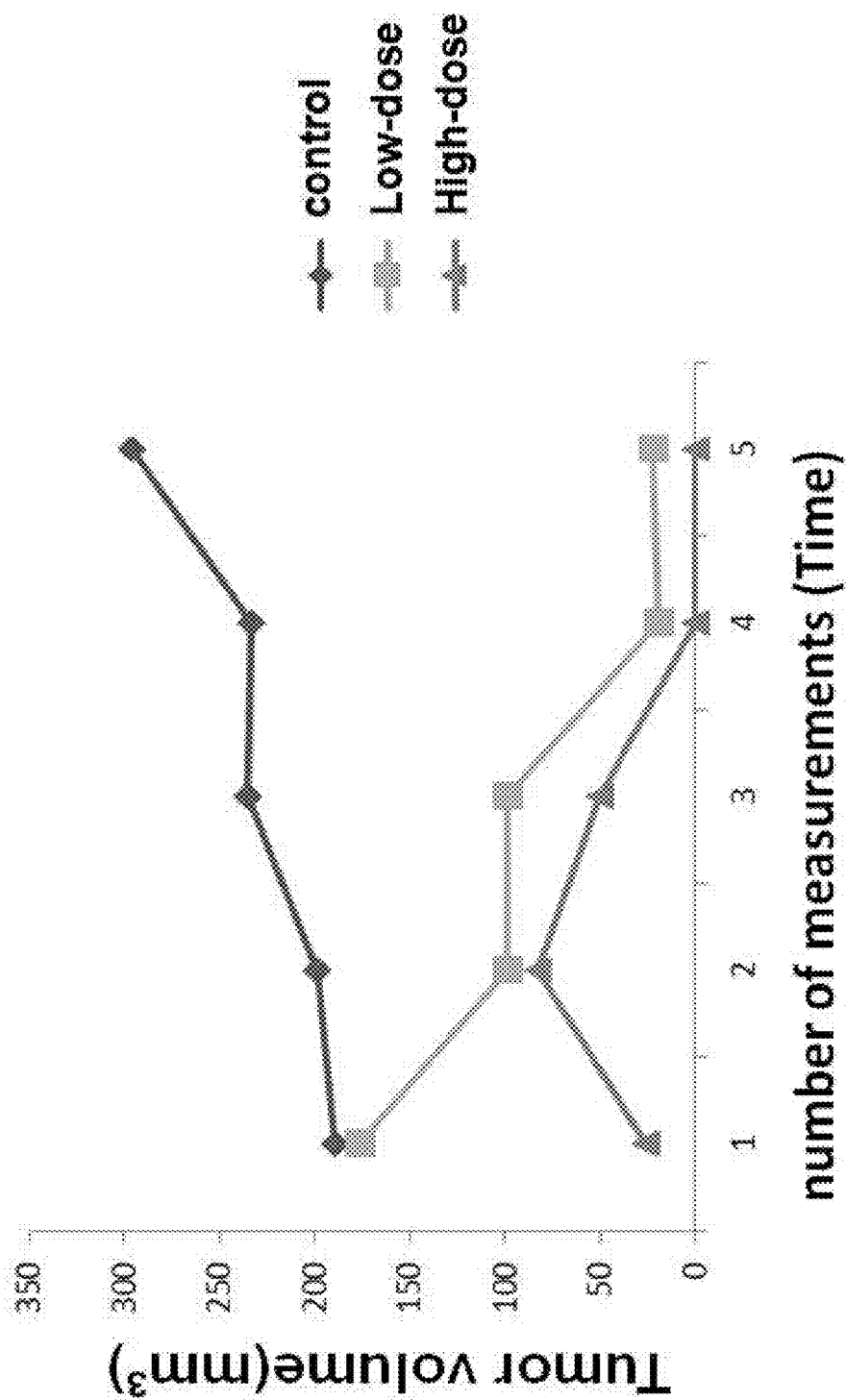
FIG. 2 shows the results of the inhibitory effect of tumor volume by Monobenzone.

According to the results in FIG. 2, both low dose and high dose of Monobenzone had significant inhibition effect on tumor cells, and the weight of mice did not show a significant decrease during the experiment. These results indicated that both high and low doses of Monobenzone could keep the tested mice in healthy status during the treatment without death.

Figure 3:
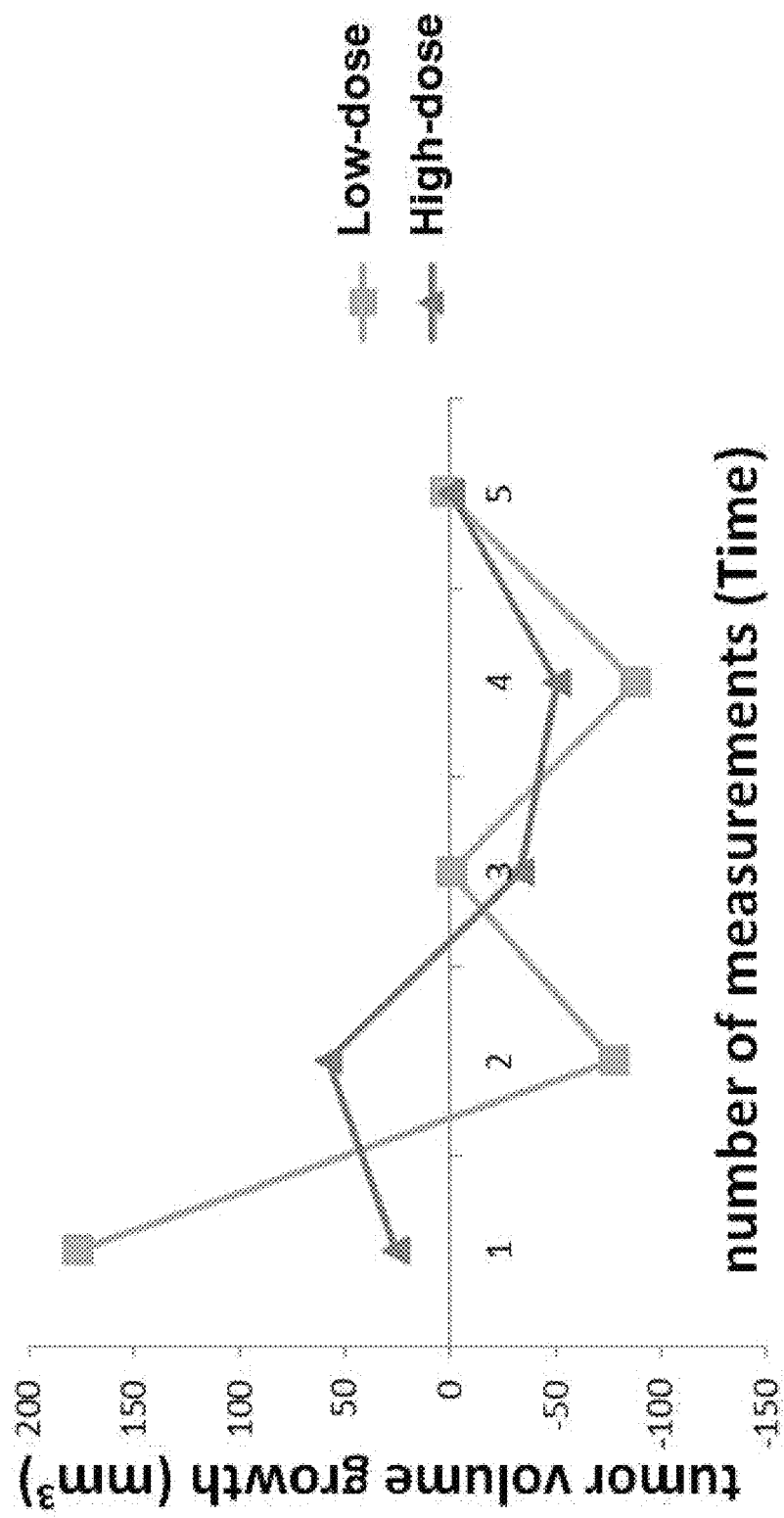
FIG. 3 shows the inhibitory effect of tumor growth via administered high-dose and low-dose of Monobenzone.

According to the results in FIG. 3, high dose of Monobenzone had effectively slow down the tumor volume growth, and can also reduce the tumor volume. Especially, high doses of Monobenzone had better effect to inhibit tumor growth.

Although the present invention has been described in terms of specific exemplary embodiments and examples, it will be appreciated that the embodiments disclosed herein are for illustrative purposes only and various modifications and alterations might be made by those skilled in the art without departing from the spirit and scope of the invention as set forth in the following claims.

What is claimed is:

1. A method for treating kidney cancer comprising: administering to a subject in need thereof a therapeutically effective amount of a pharmaceutical composition comprising Monobenzone or a pharmaceutical acceptable salt thereof.

2. The method of claim 1, wherein the effective amount of Monobenzone is from 20 mg/kg/day to 500 mg/kg/day.

* * * * *